(12) United States Patent
Maeda

(10) Patent No.: US 7,731,676 B2
(45) Date of Patent: Jun. 8, 2010

(54) URETERAL STENT

(76) Inventor: Toru Maeda, c/o Vector Company Ltd., 1-26-4, Sasazuka, Shibuya-ku, Tokyo (JP)

(*) Notice: Subject to any disclaimer, the term of this patent is extended or adjusted under 35 U.S.C. 154(b) by 538 days.

(21) Appl. No.: 11/497,245

(22) Filed: Aug. 2, 2006

(65) Prior Publication Data

US 2007/0032880 A1    Feb. 8, 2007

(51) Int. Cl.
  *A61M 37/00*    (2006.01)
  *A61M 31/00*    (2006.01)
  *A61B 17/22*    (2006.01)

(52) U.S. Cl. .................... 604/8; 604/544; 606/127

(58) Field of Classification Search ............ 604/7–10, 604/540, 544, 264; 606/153, 127
See application file for complete search history.

(56) References Cited

U.S. PATENT DOCUMENTS

| | | | | |
|---|---|---|---|---|
| 3,938,529 | A * | 2/1976 | Gibbons | 604/8 |
| 4,334,327 | A * | 6/1982 | Lyman et al. | 623/23.66 |
| 4,813,925 | A * | 3/1989 | Anderson et al. | 604/8 |
| 4,955,859 | A * | 9/1990 | Zilber | 604/8 |
| 5,222,971 | A * | 6/1993 | Willard et al. | 606/198 |
| 5,246,445 | A * | 9/1993 | Yachia et al. | 623/1.2 |
| 5,380,335 | A * | 1/1995 | Dormia | 606/127 |
| 5,599,291 | A * | 2/1997 | Balbierz et al. | 604/8 |
| 6,364,868 | B1 * | 4/2002 | Ikeguchi | 604/514 |
| 6,758,857 | B2 * | 7/2004 | Cioanta et al. | 607/105 |

* cited by examiner

*Primary Examiner*—Leslie R Deak
(74) *Attorney, Agent, or Firm*—Richard C. Litman

(57) ABSTRACT

A ureter stent designed for assisting the draining of urine with calculus fragments. The ureter stent includes a first holding portion, a second holding portion and a junction portion. The first holding portion has a pigtail shape for holding itself in a kidney. The second holding portion has a pigtail shape for holding itself in a bladder. The junction portion joins the first holding portion and the second holding portion and placed in a ureter. The junction portion is made of a metal round wire having no internal flow path. Urine flows outside the ureter stent.

16 Claims, 7 Drawing Sheets

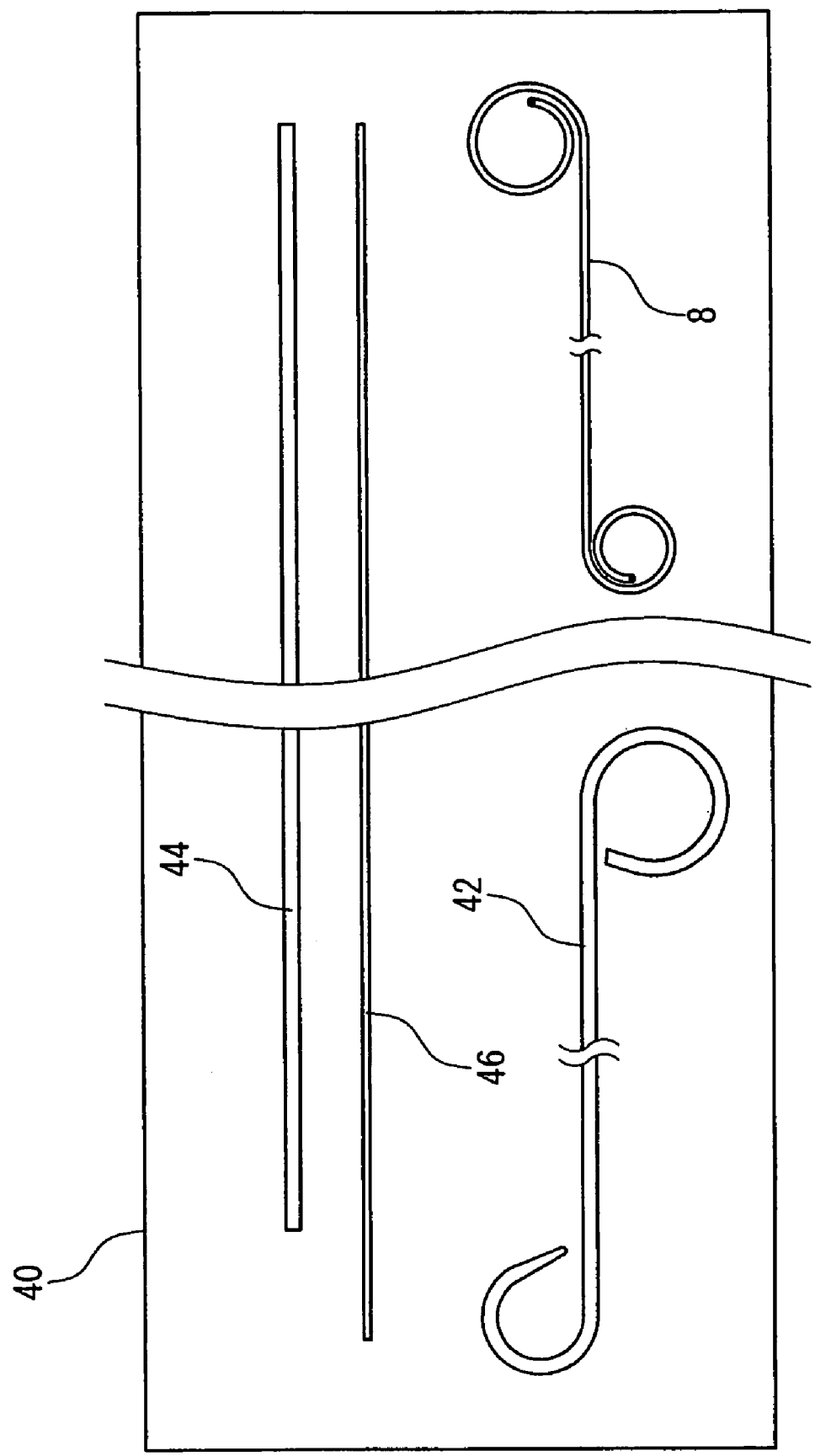

URETERAL STENT

BACKGROUND OF THE INVENTION

1. Field of the Invention

The present invention relates to a ureteral stent placed between a kidney and a bladder.

2. Description of the Related Art

A process for placing a ureteral stent in a ureter in order to protect the ureter from being narrow and reserve a flow path of urine. The ureteral stent has been requested for reducing the burden on a patient and reserving the flow path of the urine.

When a calculus appears in the kidney or ureter, a process is often performed for using ESWL (Extracorporeal Shock-Wave Litotripsy), and chopping the calculus and then discharging the chopped calculus pieces through the ureter from a body. After the calculus is chopped, the ureteral stent is placed to reserve the urine path.

Japanese Laid-Open Patent Application (JP-A-Heisei, 6-238007) discloses a ureteral stent characterized by having a lead portion, a main body and a tail portion and having a lumen therein, wherein the main body is at least constituted by a super-elastic metal tube and an outer diameter ($\phi_o$) and an inner diameter ($\phi i$) of the super-elastic metal tube are defined so as to satisfy the following equations (1) and (2).

$$\phi_o \leq 3000 \text{ μm} \quad (1)$$

$$200 \text{ μm} \leq (\phi_o - \phi_i)/2 \leq 150 \text{ μm} \quad (2)$$

PCT application WO/2002/053065 discloses a radially expanding ureteral device. The ureteral device is provided for facilitating stone passage through a ureter or duct. An exemplary ureteral device includes a flexible, elongate body that defines a plurality of cages along the body. In a contracted state the cages have a reduced diameter. When an activation force is applied, the cages transform to an expanded state, thereby defining a plurality of void spaces. The void spaces are configured to receive an obstruction, such as a stone.

Japanese Laid-Open Patent Application (JP-P2003-19211) discloses a stent. The stent is disintegrated in a living body after staying in the body for a time appropriate for a therapeutic purpose.

Japanese Patent (JP2888979-B2) discloses a stent for removing calculus and its fragments. The stent includes an elongate and flexible tube.

SUMMARY OF THE INVENTION

An object of the present invention is to provide a ureteral stent for enhancing the discharge of calculus fragments.

Another object of the present invention is to provide a ureteral stent which is preferably used even for a ureter including narrow portion.

Still another object of the present invention is to provide a ureteral stent having reduced burden on a human body.

In an aspect of the present invention, the ureteral stent includes: a first holding portion configured to prevent the stent from displacing from a kidney by hanging a junction of renal pelvis and ureter when placed in the renal pelvis; a second holding portion configured to prevent the stent from displacing from a bladder by hanging a ureterovesical junction when placed in the bladder; and a junction portion having a solid-core round wire which joins the first holding portion and the second holding portion. The longitudinal direction is substantially conforming with the ureter when placed in the ureter.

Preferably, the round wire is made of metal. The cross section of the round wire in a direction perpendicular to a longitudinal direction of the round wire forms a convex domain. The size of the round wire is equal to or less than 4 French.

Preferably, the round wire is covered by a winding wire or braided material.

In another aspect of the present invention, the ureter stent further includes an auxiliary wire fixed to the round wire at a first point and a second point. The length between the first point and the second point along the auxiliary wire is larger than the length between the first point and the second point along the round wire.

In further another aspect of the present invention, the ureter stent further includes a wavy round wire joined to the round wire at a first point near the first holding portion and at a second point near the second holding portion. The shape of the wavy round wire is waveform, the direction of the amplitude of the waveform is substantially perpendicular to a longitudinal direction of the round wire.

In further another aspect of the present invention, the junction portion includes a helical portion. The central axis of helix included in the shape of the helical portion is substantially parallel to the line connecting the junction of the junction portion and the first holding portion and the junction of the second holding portion and the junction portion.

Preferably, the area contacting with the renal pelvis surface is covered by fluoride resin.

Preferably, the surface of the ureter stent of the present invention has a chromatic stripe pattern.

Preferably, the shape of the first holding portion is a pig tail shape.

In further another aspect of the present invention, the shape of the first holding portion is helical. The central axis of the helical shape of the first holding portion is substantially parallel to a longitudinal direction of the round wire when the ureter stent is free from external force. Or the central axis of the helical shape of the first holding portion is substantially perpendicular to a longitudinal direction of the round wire when the ureter stent is free from external force.

In an aspect of the present invention, a ureter stent set includes: a ureter stent according to the present invention; a sleeve; and a pusher. The sleeve is configured to have a tube shape having an internal path through which the ureter stent is guided into a human body and the first holding portion is guided into a kidney, and the pusher is configured to push the ureter stent along the internal path.

Preferably, the ureter stent set further includes a tube-shaped second ureter stent having a flow path through which urine flows, and an external surface of the ureter stent is slidably fit into an internal path of the second ureter stent.

According to the present invention, the ureteral stent for enhancing the discharge of the calculus fragments is provided.

Also according to the present invention, the ureteral stent which is preferably used even for the ureter including narrow portion.

Also according to the present invention, the ureteral stent having reduced burden on the human body is provided.

BRIEF DESCRIPTION OF THE DRAWINGS

FIG. 12 shows a configuration of a ureteral stent system.

DESCRIPTION OF THE PREFERRED EMBODIMENTS

Figure 1:
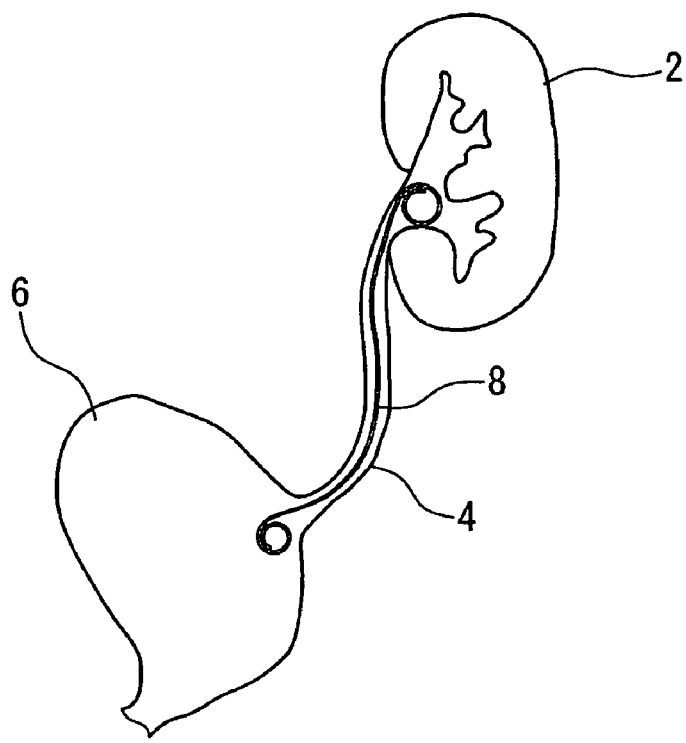
FIG. 1 shows a state where a ureteral stent is placed inside a body.

The embodiment of a ureteral stent according to the present invention will be described below with reference to the drawings. FIG. 1 shows the ureteral stent placed inside a human body. A renal pelvis of the kidney 2 is connected to an end of the ureter 4. The other end of the ureter 4 is connected to the bladder 6. The ureteral stent 8 is placed inside the ureter 4 in the state that one end is located at a space of the renal pelvis and the other end is located at a space inside the bladder.

Figure 2:
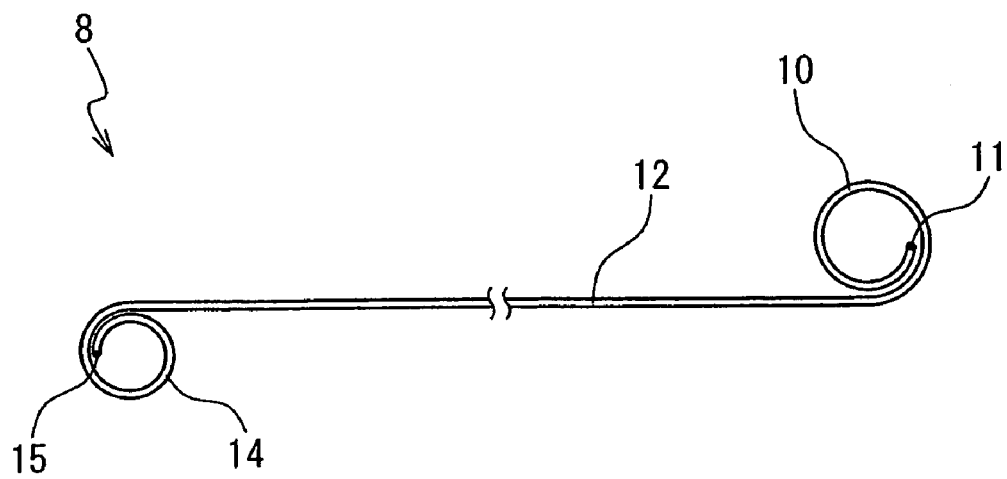
FIG. 2 shows a configuration of the ureteral stent.

FIG. 2 shows the configuration of the ureteral stent 8. The ureteral stent 8 includes a wire (called "core wire") as a main component. The wire can be made of resin. The wire can be made of resin. In this embodiment, the wire made of metal is desirable. By using metallic core wire, the load on the body of a patient is suppressed; the uncomfortable feeling sensed by the patient is small; the manufacturing process is simple; and generally stronger than the wire of same size and made of resin. Specifically, the metal that is kink-inhibiting and is resist rust is preferably adopted as the wire material. As such metals, stainless and nitinol can be preferably exemplified.

The portion near a first end 11 of the ureteral stent 8 is a first holding portion 10 that is processed to the shape of the "pig tail", namely, the shape having a curling for preventing the end from dropping out of a certain cavity inside a body and slipping out of a vessel connected to the cavity. A portion near a second end 15 of the ureteral stent 8 is a second holding portion 14 that is processed to the shape of the pig tail. The first holding portion 10 and the second holding portion 14 are connected through a connecting portion 12. By the first holding portion 10, one end of the ureteral stent 8 is hooked at the junction of renal pelvis and ureter and held inside the kidney. By the second holding portion 14, the other end of the ureteral stent 8 is hooked at a junction of ureter with bladder and held inside the bladder. As a result, the connecting portion 12 is held inside the ureter 4. Since the first holding portion 10 has the shape of the pig tail, the possible load on the body caused by the first end 11 contacting to the kidney is suppressed. Since the second holding portion 14 has the shape of the pig tail, the possible load on the body caused by the second end 15 contacting to the bladder 6 is suppressed.

Figure 3:
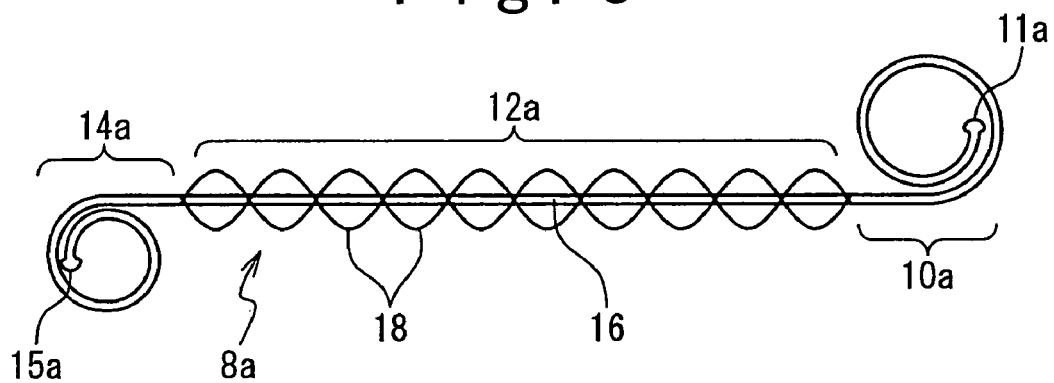
FIG. 3 shows a configuration of the ureteral stent.

The variation in the configuration of the ureteral stent 8 will be explained below with reference to FIGS. 3 to 9, 13A, 13B and 14. FIG. 3 shows a ureteral stent 8a whose surface is processed so that the surface of the core wire is covered with a wire-wrapping, mesh or braid. The ureteral stent 8a has a core wire 16. The core wire is flexible and hard to kink. The core wire remains in an elastic deformation region when the shape of the ureter 4 is deformed by the maximum motion of the human body.

The core wire 16 is a solid-core wire. Namely, it does not have therein a groove or a path where fluid (typically, urine) flows. The urine flows outside the core wire 16. The ureteral stent 8, which is made of metal and has the solid core wire, can be made strong and thin. For example, the sufficient strength and elastic force can be achieved even in the size of 4 F (4 French) or thinner. Moreover, the core wire can be made such that its diameter is 1 mm or less.

Figure 13A:
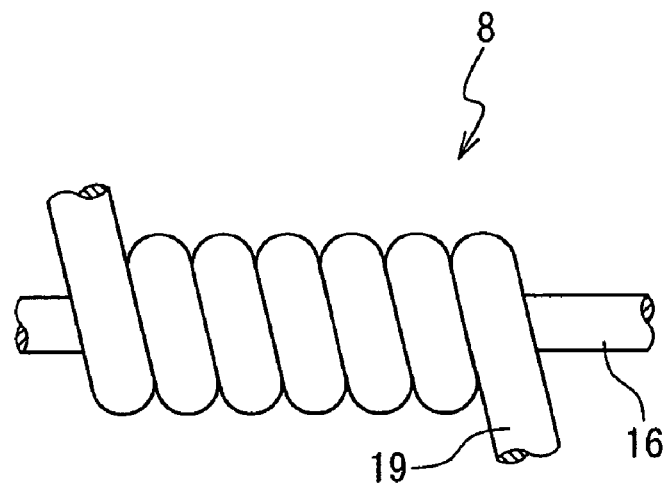
FIG. 13A shows a closeup view of the core wire.

FIG. 13A shows the closeup view of a fragmentary view of the connecting portion 12 of the ureteral stent 8. In this case, the surface of the core wire 16 is covered by an overwinding material made of a metallic round wire 19. Namely, the connecting portion is made of a wound string.

Figure 13B:
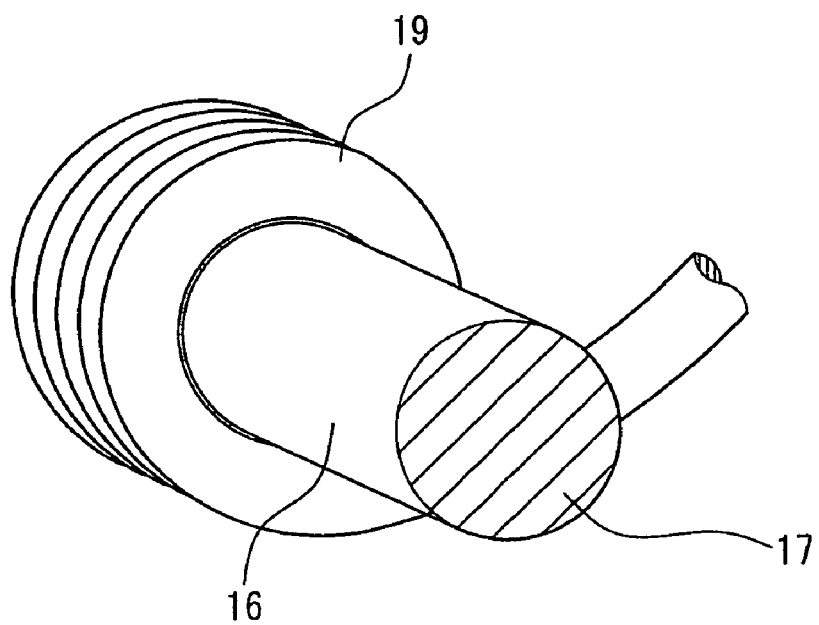
FIG. 13B shows a schematic view of the cross section of the ureteral stent.

FIG. 13B shows a cross section of the core wire 16. The core wire 16 is not a tube but a solid round wire. Preferably, the cross section 17 of the core wire 16 in a direction perpendicular to the longitudinal direction of the core wire 16 forms a convex domain. Namely, the core wire 16 has no groove or flow path on its surface thorough which the urine flows. Such a core wire is simple and strong. Also the clogging caused by the fragments of the calculus or the like is suppressed because of the convexity of the surface.

In the core wire 16, the portions near its both ends are thinner than its center portion. That is, the first holding portion 10a and the second holding portion 14a of the core wire 16 are thinner than the connecting portion 12a. When the ureter stent is placed in the ureter, because the connecting portion 12a is thicker, a stronger elastic force is generated so that the urinary flow path in the ureter is straightened and the smoothness of the ureter flow is improved. On the other hand, because the first holding portion 10a and the second holding portion 14a are thinner, the elastic force is weak and the holding portions can be deformed easily.

The portion in contact with the human body when the ureteral stent 8a is placed inside the body is coated with fluoro-resin exemplified by poly-tetra-fluoro-ethylene.

For the safety, the cut edge of the first end 11a of the core wire 16 is smoothed by welding. The portion close to the first end 11a of the ureteral stent 8a is the first holding portion 10a processed to the shape of the pig tail. The portion close to the second end 15a is the second holding portion 14a processed to the shape of the pig tail. The surface of the core wire 16 is covered by a covering wire 18 which forms a braid. In FIG. 3, the covering wire 18 is symbolically drawn. Although it is away from the core wire 16 on the drawing, it is in contact with and fixed to the core wire 16 in the actual configuration. Covered string is preferably used instead of the braid-processing. The surface of the covering wire 18 is hydrophilic. Preferably, the covering wire 18 is made of metal. The covering wire 18 is welded together with the core wire 16, at the first end 11a and the second end 15a. A stripe pattern vertical to the extension direction of the connecting portion 12a is preferred to be drawn on the surface (portion visible from outside) of the connecting portion 12a of the ureteral stent 8a.

FIG. 12 shows the configuration of the stent set 40 including the ureteral stent 8 exemplified by the ureteral stent 8a. The stent 40 contains the ureteral stent 8, a sleeve 44 and a pusher 46.

Preferably, the stent set 40 further includes a ureteral stent 42. The ureteral stent 42 is a conventional stent having a shape of a tube made of resin, having a urinary flow path therein. The inner circumference of the ureteral stent 42 slidably fits the outer circumference of the ureteral stent 8.

The ureteral stent 8a is used as follows. The calculus located in the kidney 2 or ureter 4 is fragmented by using the process such as the ESWL (Extracorporeal Shock-Wave Lithotripsy) and the like. Before or after the process, the ureteral stent 8a is guided into the body.

The ureteral stent 8a is guided into the body as follows. The sleeve 44 and pusher 46 for guiding the stent 8a are prepared. The sleeve 44 has the shape of a tube having a path both ends of which are opened. The sleeve 44 is guided from the urethra through the bladder 6 to an inlet of the kidney 2.

The ureteral stent 8a is guided by the path of the sleeve 44 and introduced into the urethra from the external urinary meatus side. At this time, the first holding portion 10 and the second holding portion 14 are elastically deformed and become the shapes along the path of the sleeve 44. Following to the ureteral stent 8a, the pusher 46 is inserted into the path of the sleeve 44 from the external urinary meatus side. In the path of the sleeve 44, the ureteral stent 8a is pushed by the pusher 46 and moved toward the kidney along the sleeve 44. Since the surface of the ureteral stent 8a is coated with fluoride, the friction is small and the ureteral stent 8a smoothly moves along the path of the sleeve.

Pushed by the pusher 46, the first holding portion 10a goes outside the sleeve 44 (inside the kidney) from the end of the sleeve 44. The first holding portion 10a is elastically deformed and returns to the shape of the pig tail. The sleeve 44 is pulled out from the side of the urethra. The ureteral stent 8a is hooked by an outlet of the kidney to the ureter 4 and remains at that position. When the sleeve 44 is pulled out, the second holding portion 14a is elastically deformed and returns to the shape of the pig tail and remains in the bladder 6. In this way, the ureteral stent 8a is placed. If the stripe pattern is drawn on the surface of the connecting portion 12a, the insertion depth of the ureteral stent 8a guided into the ureter can be easily recognized.

The longitudinal direction of the core wire 16 is substantially conforming with the ureter when the ureteral stent 8a is placed in the renal pelvis.

The operation of the ureteral stent 8a is explained as follows. The elastic force of the connecting portion 12a causes the ureter 4 to approach the shape of a straight line. This makes the flow of the urine smoother. Moreover, the ingredients or the fragmented pieces of the calculus included in the urine are easy to flow. Moreover, since the covering wire 18 is installed, a lot of gaps are existed in the portion where the ureteral stent 8a (having hydrophilic surface) and the ureter are in contact with each other, and the urine flows more smoothly.

The ureteral stent 8a is not hollow but solid. A flow path does not exist in the center of the ureteral stent 8a. Thus, the cross section of the ureter 4 outside the stent is larger than that of the hollow stent, supposing that the amount of the substance included in the solid ureteral stent 8a is same with that of the hollow stent. Hence, the ingredients and the fragmented pieces of the calculus are easy to flow. In particular, the relatively large calculus and fragmented pieces are easy to flow.

Conventionally, the ureteral stent 42 that has a tube shape, namely, having the path in which the urine flows is usually used. After the ureteral stent 8a of this embodiment is placed in the body, if there is a need to exchange the stent 8a for the conventional ureteral stent 42, the second holding portion 14 of the ureteral stent 8a is pulled outside the body from the urethra, and the flow path placed in the core of the conventional ureteral stent 42 is fitted with the ureteral stent 8a. And the ureteral stent 42 is inserted into the body guided by the ureteral stent 8a and placed in the renal pelvis. After that, the ureteral stent 8a is extracted from the external edge of the ureteral stent 42. That is, since the ureteral stent 8a can be used as the guide, the exchanging procedure is easy, which reduces the load on the patient. For this reason, the ureteral stent 8a is preferred to be used as the stent system 40 including the conventional ureteral stent 42.

Figure 14:
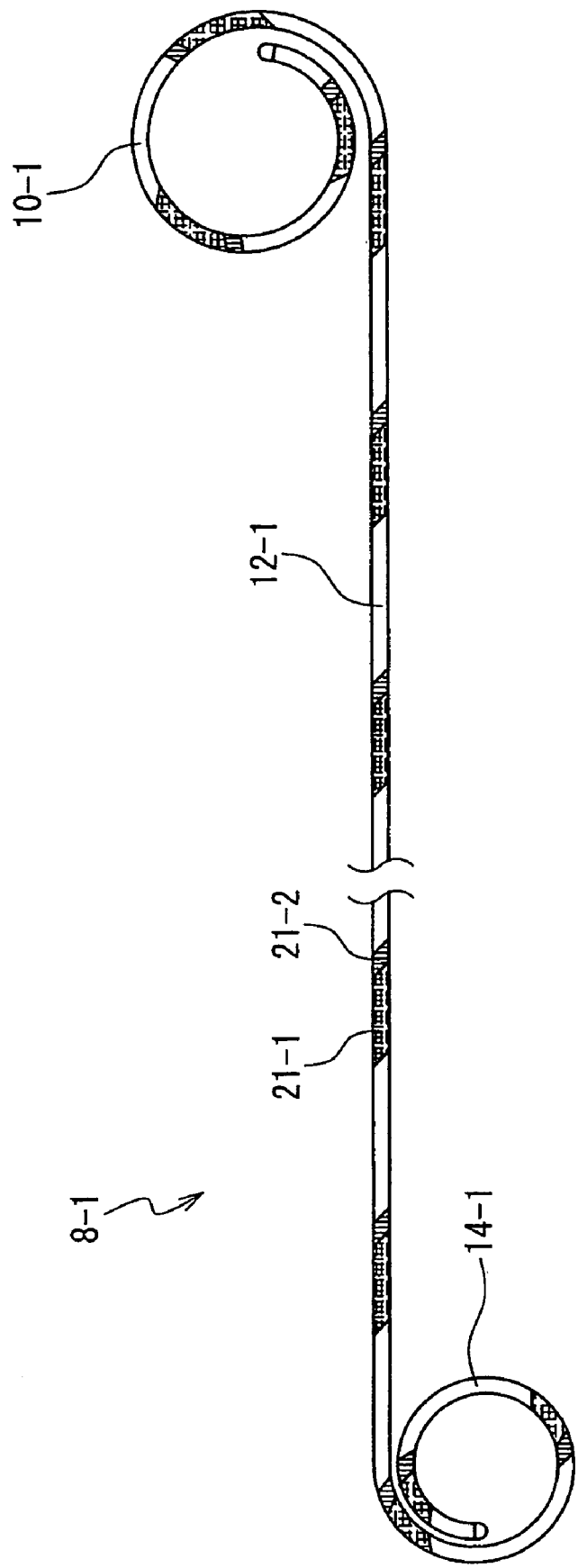
FIG. 14 shows a configuration of a ureteral stent having stripe pattern.

FIG. 14 is another example of the ureteral stent 8-1. The connecting portion 12-1, the first holding portion 10-1 and the second holding portion 14-1 which are made of a single core wire. The surface of the core wire has colored zones. The colored zones are placed periodically in the length direction of the core wire. Each of the color zones has a first color zone 21-1 and a second color zone 21-2. They are placed adjacently in the length direction. The color of the second color zone 21-2 is different from that of the first color zone. For using the ureteral stent having such colored zones, in inserting to or withdrawing from the body, it is easy for the doctor to recognize the inserting depth of the ureteral stent.

Figure 4:
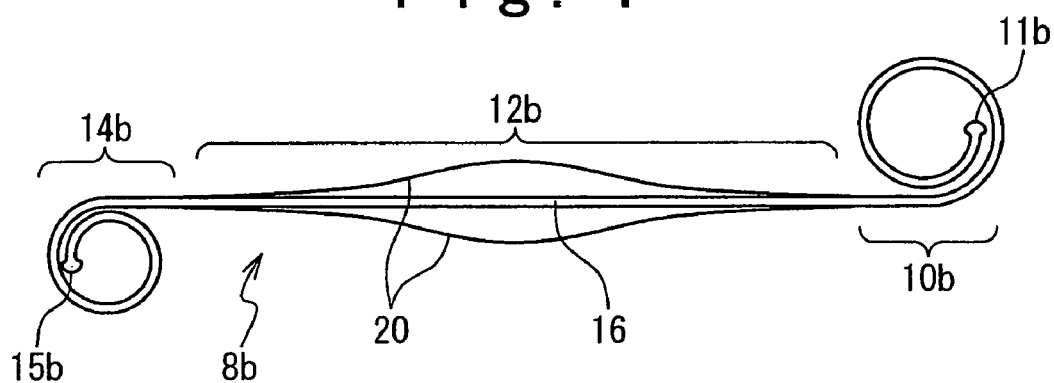
FIG. 4 shows a configuration of the ureteral stent.

Another configuration of the ureteral stent 8 will be described below with reference to FIGS. 4 to 9. FIG. 4 shows a ureteral stent 8b having auxiliary wires. The ureteral stent 8b has the core wire 16 similar to that of FIG. 3. The ureteral stent 8b further has auxiliary wires 20. One end of the auxiliary wire 20 is welded together with the core wire 16, in a first end 11b. The other end is welded together with the core wire 16 in a second end 15b. The auxiliary wire 20 is longer than the core wire 16. That is, the length along the auxiliary wire 20 between the first end 11b and the second end is larger than the length along the core wire 16. Connected to the core wire 16 in both ends, the auxiliary wire 20 is elastically deformed so that the shape of the auxiliary wire 20 is convex.

The position where the auxiliary wire 20 is fixed to the core wire 16 can be also set as follows. That is, one end of the auxiliary wire 20 is fixed at the junction of the first holding portion 10b and the connecting portion 12b, and the other end is fixed at the junction of the second holding portion 14b and the connecting portion 12b.

Preferably, two or more auxiliary wires 20 are connected to the core wire 16. In the case of the two auxiliary wires 20, when any external force is not applied, it is desirable that the two auxiliary wires 20 are connected to the core wire 16 so that the core wire 16 and the two auxiliary wires are placed on the same flat surface. Namely, the first auxiliary wire and the second auxiliary wire are connected to the core wire 16 at the sides opposite to each other.

According to the ureteral stent 8b, the ureter 4 is pushed and spread by the elastic force of the auxiliary wire 20, and wide path for the urine flow is maintained. The portions where the plurality of auxiliary wires 20 are convex are moved independently of each other. For example, in the renal pelvis, when the first auxiliary wire 20 is convex in the portion near the first holding portion 10b, the second auxiliary wire 20 is convex in the portion near the second holding portion 14b. Such deformation reserves the urine path while protecting the excessive force from being applied to the ureter 4.

Figure 5:
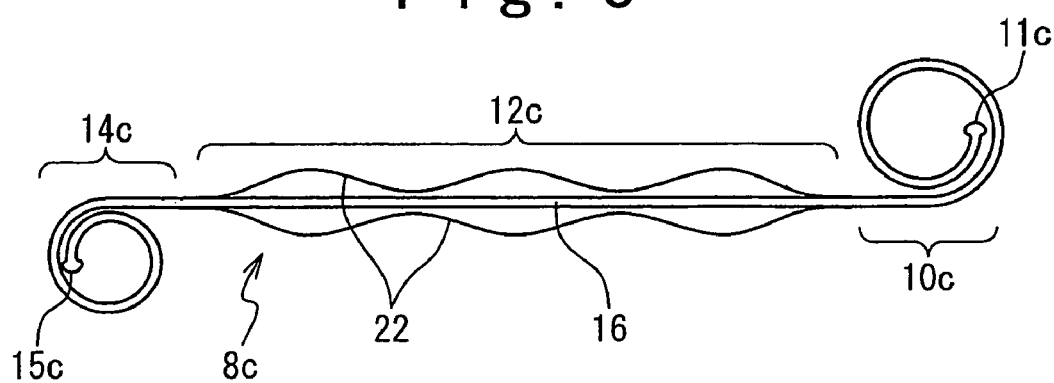
FIG. 5 shows a configuration of the ureteral stent.

FIG. 5 shows a ureteral stent 8c having wave-shaped auxiliary wires. The ureteral stent 8c has the core wire 16 similar to that of FIG. 3. The ureteral stent 8c further has auxiliary wires 22 each of which is made of round wire. One end of the auxiliary wire 22 is welded together with the core wire 16 in a first end 11c. The other end is welded together with the core wire 16 in a second end 15c. When the core wire 16 is straightly extended, the auxiliary wire 22 is wave-shaped.

The position where the auxiliary wire 22 is fixed to the core wire 16 can be also set as follows. That is, one end of the auxiliary wire 22 is fixed to the junction of the first holding portion 10c and the connecting portion 12c, and the other end is fixed to the junction of the second holding portion 14c and the connecting portion 12c.

Two or more auxiliary wires 22 are preferred to be installed. In the case that the number of the auxiliary wires 22 is two, when the force is not applied, the core wire 16 and the two auxiliary wires 22 are preferred to be installed so as to be located on the same flat surface.

Such a ureteral stent 8c provides the effect similar to the ureteral stent 8b in FIG. 4. From the viewpoint of protecting the urine path from being narrow in any portion of the ureter 4, the configuration that the auxiliary wire 22 is wave-shaped is preferable.

Figure 6:
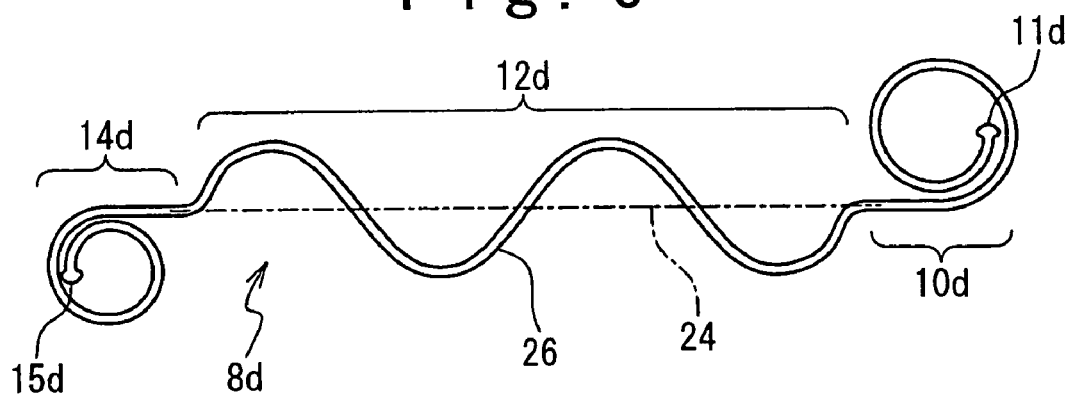
FIG. 6 shows a configuration of the ureteral stent.

FIG. 6 shows a ureteral stent 8d having a helical wire. The ureteral stent 8d has the helical shape which is centered on a central line 24 for connecting: a point where a first holding portion 10d and a connecting portion 12d are linked; and a point where the connecting portion 12d and a second holding portion 14d are linked, when external force is not applied.

With the ureteral stent 8c, the ureter 4 is held in the shape close to a cylindrical shape, and the urine path is maintained in a desirable shape.

Figure 7:
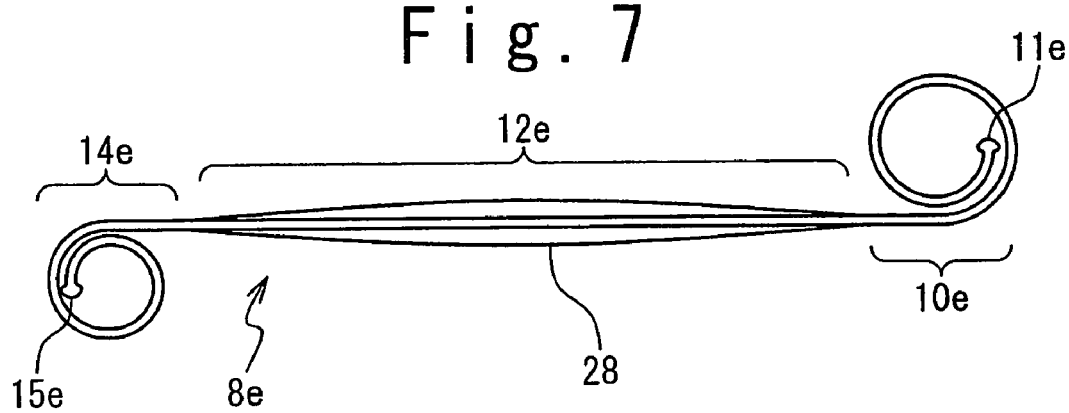
FIG. 7 shows a configuration of the ureteral stent.

FIG. 7 shows a ureteral stent 8e having a plurality of thin wires along the core wire. The ureteral stent 8e has a plurality of thin wires 28. The plurality of wires 28 and the core wire are welded together in a first end 11e. Moreover, the plurality of wires 28 and the core wire are welded together in a second end 15e. When the plurality of wires 28 are straightly extended, they are in line contact with each other.

In such a ureteral stent 8e, when the plurality of wires 28 are bundled, the size is preferred to be 4 frenches or less. A diameter is further preferred to be 1 mm or less. Since the diameter is small, the cross section of the ureter 4 outside the ureteral stent 8e is large, and the calculus piece is easy to flow. Moreover, since the urine can flow along each surface of the plurality of wires 28, even the inside of the ureteral stent 8e can be used as the urine path.

Figure 8:
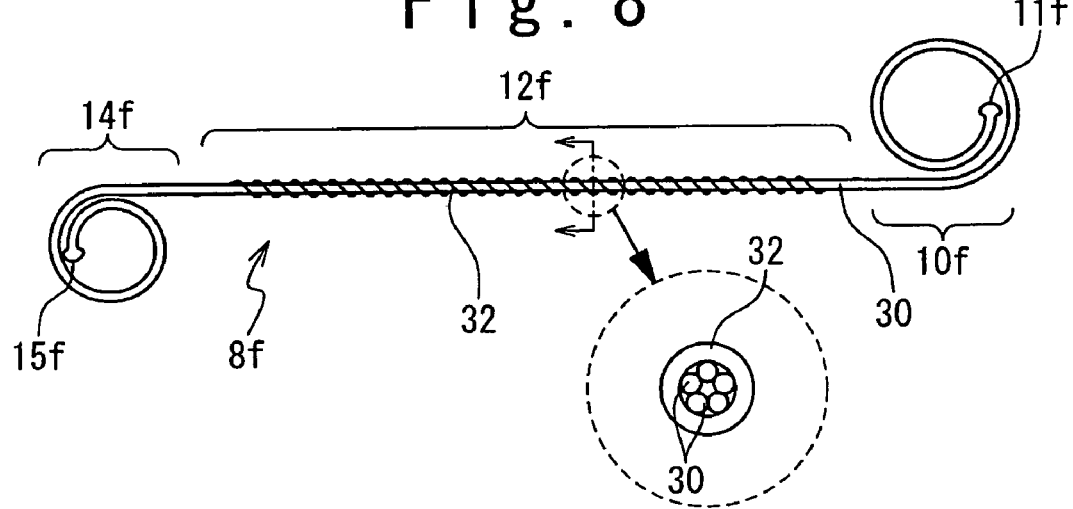
FIG. 8 shows a configuration of the ureteral stent.

FIG. 8 shows a ureteral stent 8f having a plurality of thin core wires and wirings wrapping the core wires. The ureteral stent 8f contains a plurality of wires 30 instead of the core wire 16 shown in FIG. 3. The plurality of wires 30 are fixed together in a first end 11f and a second end 15f. Moreover, the ureteral stent 8f has a wiring 32 for spirally covering the plurality of wires 30. Braid-processing covering the bundle of the plurality of wires 30 may be employed instead of the wiring 32. Such a ureteral stent 8f has a strong elastic force, and its inside can be used as a urine path.

Figure 9:
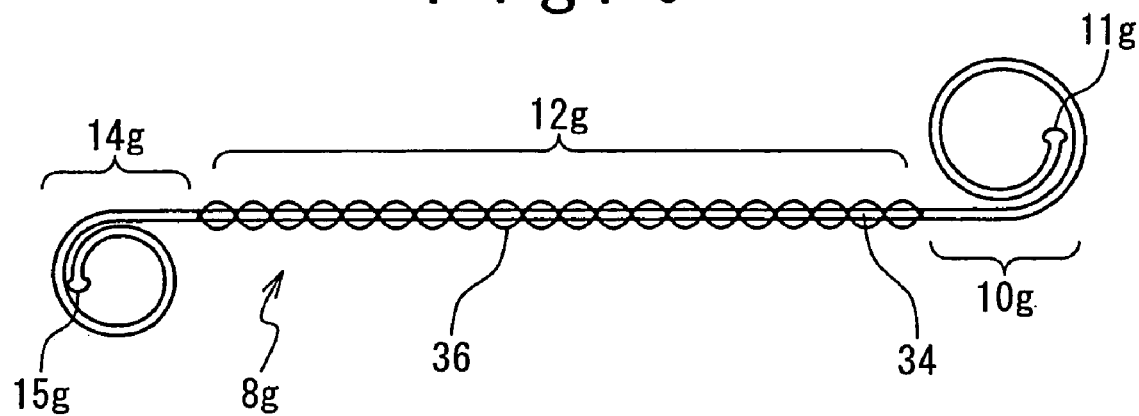
FIG. 9 shows a configuration of the ureteral stent.

FIG. 9 shows a ureteral stent 8g. The ureteral stent 8g has a core tube having a flow path therein. The surface of the ureteral stent 8g is mesh-processed. The ureteral stent 8g has a wire 34 that is made of metal and has the shape of a hollow tube. The wire 34 has a first end 11g and a second end 15g. The wire 34 is covered by a covering wire 36 that is a braid-processed wire. The covering wire 36 is preferred to be made of metal.

In the ureteral stent 8g, its inside is reserved as the urine path. With the covering wire 36, the urine path is reserved even at a position where the ureteral stent 8g and the ureter 4 are in contact. The configuration that the wire 34 is made of the metal provides the effect that the uncomfortable feeling and load when it is placed inside the body is reduced.

Figure 10:
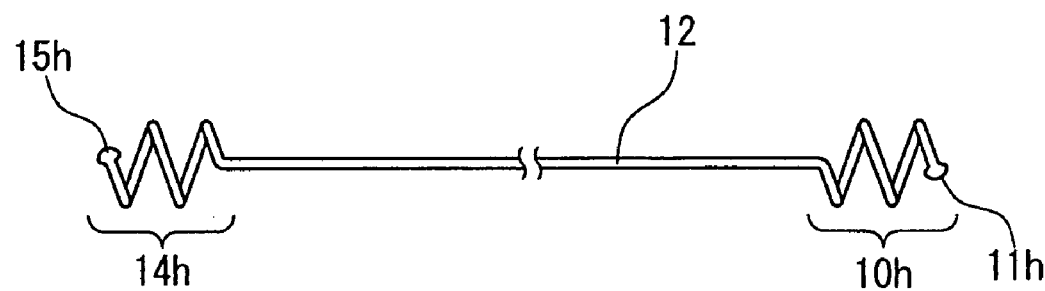
FIG. 10 shows a configuration of the ureteral stent.

FIG. 10 shows an example of a ureteral stent, in which both ends do not have the shape of the pig tail. The ureteral stent has a first holding portion 10h and a second holding portion 14h each of which is connected to an end of the connecting portion 12 including the core wire. The first holding portion 10h and the second holding portion 14h are spiral-shaped (coil-shaped). A connection point between the first holding portion 10h and the connecting portion 12 is assumed to be a first point, and a connection point between the connecting portion 12 and the second holding portion 14h is assumed to be a second point. When the external force is not applied, a first relative angle that is an angle between a central line for connecting the first point and the second point and the central axis of the coil shape of the first holding portion 10h is approximately 0 degree (namely, parallel). When the external force is not applied, a second relative angle that is an angle between the central line for connecting the first point and the second point and the central axis of the coil shape of the second holding portion 14h is approximately 0 degree (namely, parallel). The first end 11h opposite to the first point of the first holding portion 10h is welded and processed for reducing the load on the human body. The second end 15h opposite to the second point of the second holding portion 14h is welded and processed for reducing the load on the human body.

Figure 11:
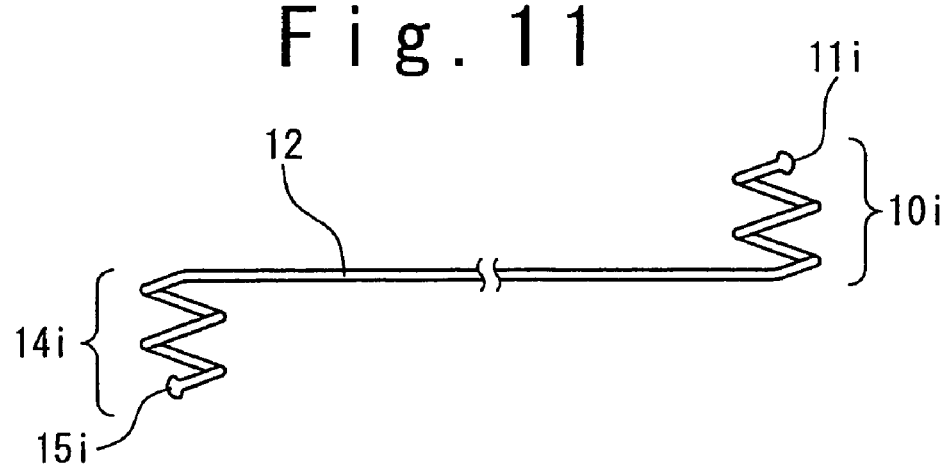
FIG. 11 shows a configuration of the ureteral stent.

FIG. 11 shows another configuration of the ureteral stent in which both ends do not have the shape of the pig tail. The ureteral stent has a first holding portion 10i and a second holding portion 14i each of which is connected to an end of the connecting portion 12 including the core wire. The first holding portion 10i and the second holding portion 14i are spiral-shaped (coil-shaped). A connection point between the first holding portion 10i and the connecting portion 12 is assumed to be a first point, and a connection point between the connecting portion 12 and the second holding portion 14i is assumed to be a second point. When the external force is not applied, a first relative angle that is an angle between a central line for connecting the first point and the second point and the central axis of the coil shape of the first holding portion 10i is approximately 0 degree (namely, vertical). When the external force is not applied, a second relative angle that is an angle between the central line for connecting the first point and the second point and the central axis of the coil shape of the second holding portion 14i is approximately 0 degree (namely, parallel). The first end 11i opposite to the first point of the first holding portion 10i is welded and processed for reducing the load on the human body. The second end 15i opposite to the second point of the second holding portion 14i is welded and processed for reducing the load on the human body.

The ureteral stent shown in FIG. 10 or 11 is easy to process. Moreover, with the first holding portions 10h, 10i and the second holding portions 14h, 14i, the ureteral stent is placed inside the ureter, and the load on the human body is reduced for the sake of the elastic force of the coil. The first relative angle and the second relative angle are properly adjusted between 0 and 90 degrees, independently of each other. At least one of the first holding portions 10h, 10i and the second holding portions 14h, 14i can be replaced by the shape of the pig tail. In the ureteral stent of FIGS. 10 or 12, the configuration of the connecting portion 12 can be replaced by the configuration of the connecting portions 12a to 12g shown in FIGS. 3 to 9.

The method of manufacturing the ureteral stent 8a shown in FIG. 3 will be described below.

(1) A wire rod which is used as the material for core wire 16 is cut to a predetermined length.

(2) The first holding portion 10a and second holding portion 14a of the core wire 16 are polished with a grindstone and shaved thinly to reduce the cross section.

(3) Covering the core wire by the covering wire 18.

(4) The first end 11a and the second end 15a are welded. The welding is carried out, for example, by using gas weld. A thermal treatment that uses plasma ion is also preferable.

(5) The core wire 16 is inserted into a die by which the first end 11a and the second end 15a are elastically deformed and hold in the shape of pig tail respectively, and their shapes are fixed in a sintering furnace.

(6) The ureteral stent 8*a* having double pig tails is sealed in a pack and shipped after the surface is checked and sterilized.

The ureteral stent made through the above mentioned method is hard to cut and kink because the first holding portion 10*a*, the second holding portion 14*a* and the connecting portion 12*a* are coupled through the integral core wire 16.

What is claimed is:

1. A ureteral stent set comprising:
   a ureteral stent;
   a sleeve; and
   a pusher,
   wherein said ureteral stent includes:
   a first holding portion configured to prevent the stent from displacing from a kidney by hanging a junction of renal pelvis and ureter when placed in the renal pelvis;
   a second holding portion configured to prevent the stent from displacing from a bladder by hanging a ureterovesical junction when placed in the bladder; and
   a junction portion having a solid-core round wire which joins said first holding portion and said second holding portion,
   wherein a longitudinal direction of said round wire is substantially conforming with the ureter when placed in the ureter, and
   a tube-shaped second ureteral stent having a flow path through which urine flows, said second ureteral stent having a first holding portion configured to prevent the second stent from displacing from a kidney and a second holding portion configured to prevent the second stent from displacing from a bladder, said second stent being sized to allow the external surface of said ureteral stent is slidably fit into an internal path of said second ureteral stent; and
   said sleeve is configured to have a tube shape having an internal path through which said ureteral stent is guided into a human body and said first holding portion is guided into a kidney, and
   said pusher is configured to push said ureteral stent along said internal path.

2. The ureteral stent according to claim 1, wherein said round wire is made of metal.

3. The ureteral stent according to claim 1, wherein a cross section of said round wire in a direction perpendicular to a longitudinal direction of said round wire forms a convex domain.

4. The ureteral stent according to claim 1, wherein a size of said round wire is equal to or less than 4 French.

5. The ureteral stent according to claim 1, wherein said round wire is covered by a winding wire.

6. The ureteral stent according to claim 1, wherein said round wire is covered by braided material.

7. The ureteral stent according to claim 1, further comprising an auxiliary wire fixed to said round wire at a first point and a second point, and a length between said first point and said second point along said auxiliary wire is larger than a length between said first point and said second point along said round wire.

8. The ureteral stent according to claim 1, further comprising:
   a wavy round wire joined to said round wire at a first point near said first holding portion and a second point near said second holding portion, and
   a shape of said wavy round wire is waveform, a direction of an amplitude of said waveform is substantially perpendicular to a longitudinal direction of said round wire.

9. The ureteral stent according to claim 1, wherein said junction portion includes a helical portion,
   wherein a central axis of helix included in the shape of said helical portion is substantially parallel to a line connecting a junction of said junction portion and said first holding portion and a junction of said second holding portion and said junction portion.

10. The ureteral stent according to claim 1, wherein said junction portion includes a second wire which is made of metal and parallel contacts parallel with said round wire when said round wire is straightened.

11. The ureteral stent according to claim 1, wherein an area of a surface of said ureteral stent is covered by fluoride resin.

12. The ureteral stent according to claim 1, wherein a surface of said ureteral stent has colored zones arranged in a length direction of said ureteral stent.

13. The ureteral stent according to claim 1, wherein a shape of said first holding portion is a pig tail shape.

14. The ureteral stent according to claim 1, wherein a shape of said first holding portion is helical.

15. The ureteral stent according to claim 14, wherein a central axis of said helical shape of said first holding portion is substantially parallel to a longitudinal direction of said round wire when said ureteral stent is free from external force.

16. The ureteral stent according to claim 14, wherein a central axis of said helical shape of said first holding portion is substantially perpendicular to a longitudinal direction of said round wire when said ureteral stent is free from external force.

* * * * *